US00PP20550P2

(12) United States Plant Patent
Moon

(10) Patent No.: US PP20,550 P2
(45) Date of Patent: Dec. 15, 2009

(54) NUTTALL OAK TREE NAMED 'QNMTF'

(50) Latin Name: *Quercus nuttalli*
Varietal Denomination: QNMTF

(75) Inventor: Dwayne C. Moon, Loganville, GA (US)

(73) Assignee: Southern Slections, LLC, Loganville, GA (US)

( * ) Notice: Subject to any disclaimer, the term of this patent is extended or adjusted under 35 U.S.C. 154(b) by 159 days.

(21) Appl. No.: 11/818,773

(22) Filed: Jun. 15, 2007

(51) Int. Cl.
*A01H 5/00* (2006.01)

(52) U.S. Cl. ..... Plt./225
(58) Field of Classification Search ..... Plt./225
See application file for complete search history.

(56) References Cited

U.S. PATENT DOCUMENTS

PP13,524 P3 1/2003 Strickland

*Primary Examiner*—Kent L Bell
(74) *Attorney, Agent, or Firm*—Polster, Lieder, Woodruff & Lucchesi, LC

(57) ABSTRACT

A Nuttall oak tree (*Quercus nuttallii*) named 'QNMTF' having a compact habit with dense canopy, vigorous growth rate, burgundy new growth that matures to dark green in summer, orange-red color in fall and also capable of being reproduced reliably from vegetative cuttings.

8 Drawing Sheets

Latin name of genus and species: *Quercus nuttallii.*
Varietal denomination: Nuttall oak tree which I have named 'QNMTF'.

BACKGROUND OF THE INVENTION

The present invention relates to a new and distinct variety of Nuttall oak tree (*Quercus nuttallii*), which I have named 'QNMTF.'

Discovery

I discovered my new tree in the spring of 2003 growing as a seedling in a production field at Moon's Tree Farm, Inc. in Loganville, Walton County, Ga. among a group of cultivated Nuttall oak trees. These trees were grown from bare-root seedlings purchased in the winter of 2001 from a nursery in Florida. In the winter of 2002, these liners were relocated from my liner field to a production field. It was here that I discovered the claimed cultivar 'QNMTF'. Evaluation of this tree continues in this field in Walton County, Loganville, Ga.

Propagation

'QNMTF' was asexually propagated by the method of vegetative cutting at my direction in the summer of 2004 at Moon's Tree Farm in Loganville, Walton County, Ga. Softwood cuttings three to five inches long were treated with 3000 ppm potassium indole-3-butyric acid (KIBA). The cuttings were then placed in peat pots filled with horticultural growing media and then intermittently misted for a period of five to six weeks. This propagation from softwood cuttings and resulting progeny has proven the characteristics of my new variety to be genetically stable. Furthermore, these observations have confirmed that my new variety represents a new and improved variety of Nuttall oak tree as particularly evidenced by the compact habit with dense canopy, vigorous growth rate and burgundy new growth that matures to dark green in summer and then orange-red fall color.

These genetic traits can be consistently reproduced by asexual propagation.

Uniqueness

'QNMTF' was discovered in a block of seedling Nuttall oak trees purchased from a supplier of liners in Florida. I claim that the genetic characteristics of this tree are the result of naturally occurring cross-pollination. Due to the nature of the seedling purchase, comparison of surrounding cross pollinators is not known. The characteristics of my new tree distinguish it from other typical seedling Nuttall oak trees and the known cultivars. At the time this tree was selected, I observed my 'QNMTF' Nuttall oak tree as a 2" caliper tree exhibiting a compact, dense canopy, dominant central leader and burgundy new foliage that matured to a dark green. The remainder of the trees in this block had irregular structure and medium green foliage color.

Use

'QNMTF' was observed for a period of several years and is believed to be particularly useful for street tree planting and in large areas such as golf courses, commercial sites and parks. 'QNMTF' will also benefit growers who will profit from a fast growing tree with consistent form.

SUMMARY OF THE INVENTION

Background

A Nuttall oak tree is native to the Mississippi Delta region as far north as southeastern Missouri and from east Texas to central Alabama. It thrives in the heat and humidity of the Southeast and can be found in bottomlands, floodplains and their adjacent slopes. Nuttall oak trees prefer moist, well-drained soils in these areas but adapts readily to harsh conditions. This species is typically pyramidal-shaped in youth and develops a rounded canopy at maturity with a typical height of 40 to 60 feet and comparable width, but can reach 100 feet or more in nature. My new cultivar differs from the species in that it is asexually reproduced, has a compact habit, dense canopy, dominant central leader and pronounced foliage colors, namely burgundy new foliage that matures to a dark green. The ultimate height and width of 'QNMTF' is not known. I expect my new variety of Nuttall oak tree 'QNMTF'to perform as well as the species.

Industry Representation

A cultivated Nuttall oak tree is predominantly represented in the industry by seedling material reproduced by an acorn. This accounts for a high degree of variability in the industry, both in the landscape and nursery. A seedling Nuttall oak tree is variable in growth rate and habit, typically has a central leader, and tends to be open in youth. The only commercially available cultivar Nuttall oak tree that I currently am aware of is *Quercus nuttailli* 'QNFTA' U.S. Plant Pat. No. 13524. This cultivar has an upright pyramidal habit with dense branching and red-orange-yellow fall color. The present cultivar 'QNMTF' differs from *Quercus nuttallii* 'QNFTA' U.S. Plant Pat. No. 13524 in that 'QNMTF' has a more vertical habit and distinct foliage color of burgundy in spring, dark green in summer and orange-red in autumn. My selection in the spring of 2006 had a 6.25" inch caliper measured at 12" inches above the ground with a height of 24' feet and a width of 13' feet giving it a 1.85 to 1 height to width ratio. *Quercus nuttallii* 'QNFTA' U.S. Plant No. 13524 has 10" caliper measured at 12" above the ground has a height of 27" feet and a width of 18' feet giving it a 1.44 1.5 to 1 height to width ratio based on its patent description. This form difference, along with unique foliage colors makes my selection uniquely different from all known patent selections and seedlings.

BRIEF DESCRIPTION OF THE DRAWINGS

The accompanying photographs depict the color of the tree and foliage of my new Nutall oak tree as nearly as is reasonably possible to make the same in a color illustration of this character.

DETAILED DESCRIPTION

Detailed Botanical Description

Figure 1:
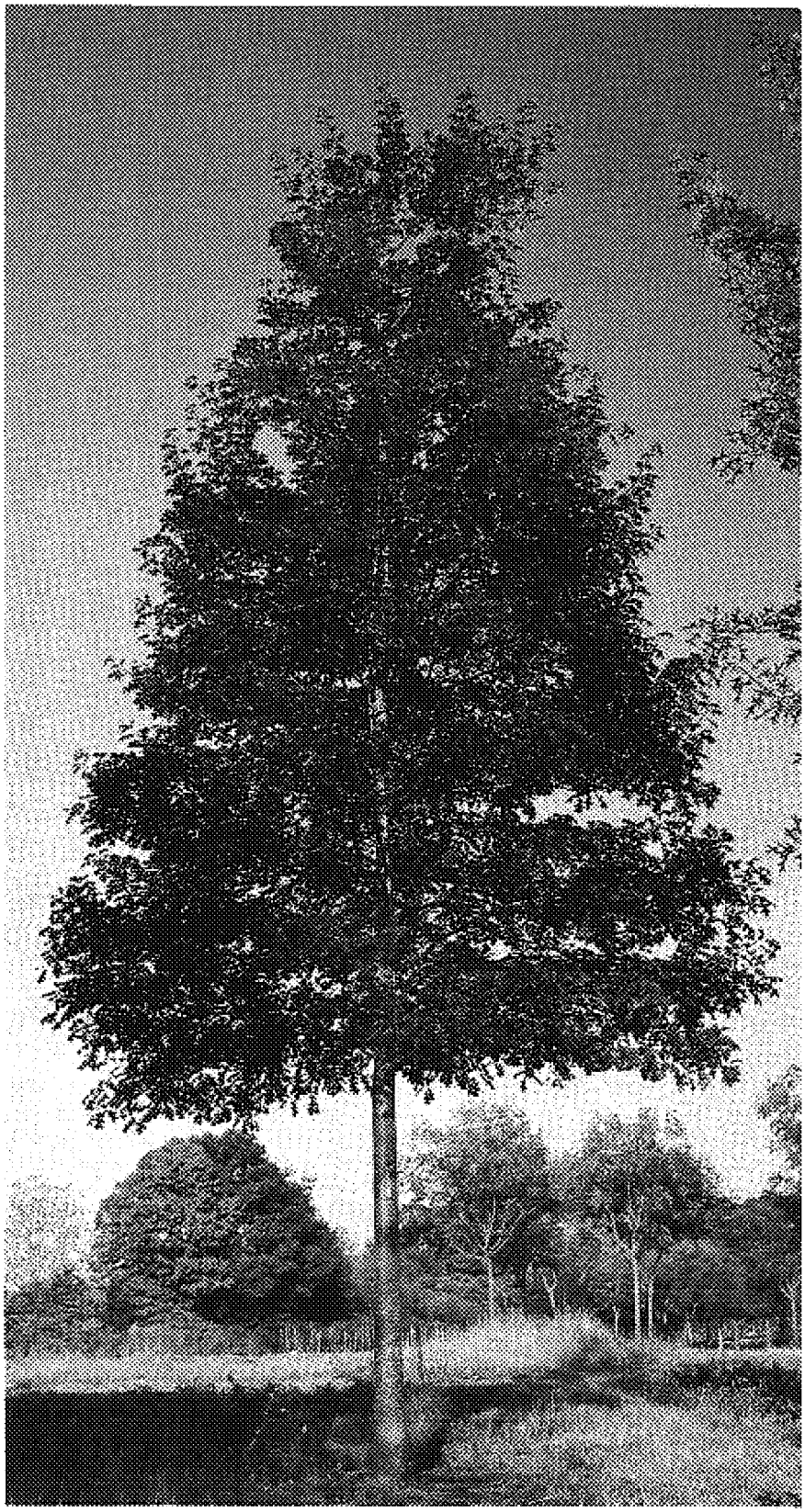
FIG. 1 taken in the production field of Walton County, Loganville, Ga. in March 2006 shows the claimed cultivar.
Figure 2:
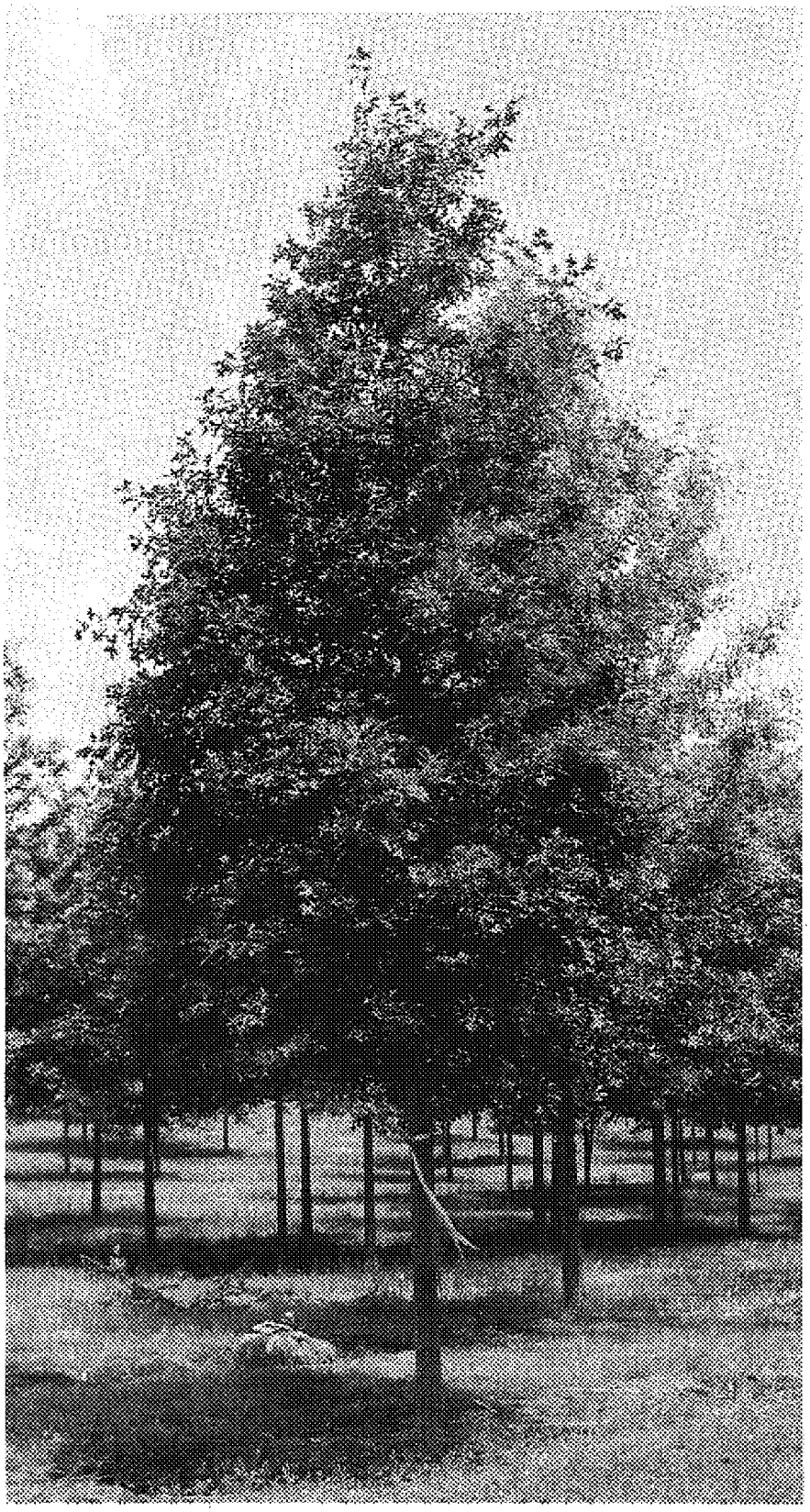
FIG. 2 taken in the production field in June 2006, shows the dark green foliage of the claimed cultivar compared to the lighter green of other seedling Nuttall oak trees in the background.
Figure 3:
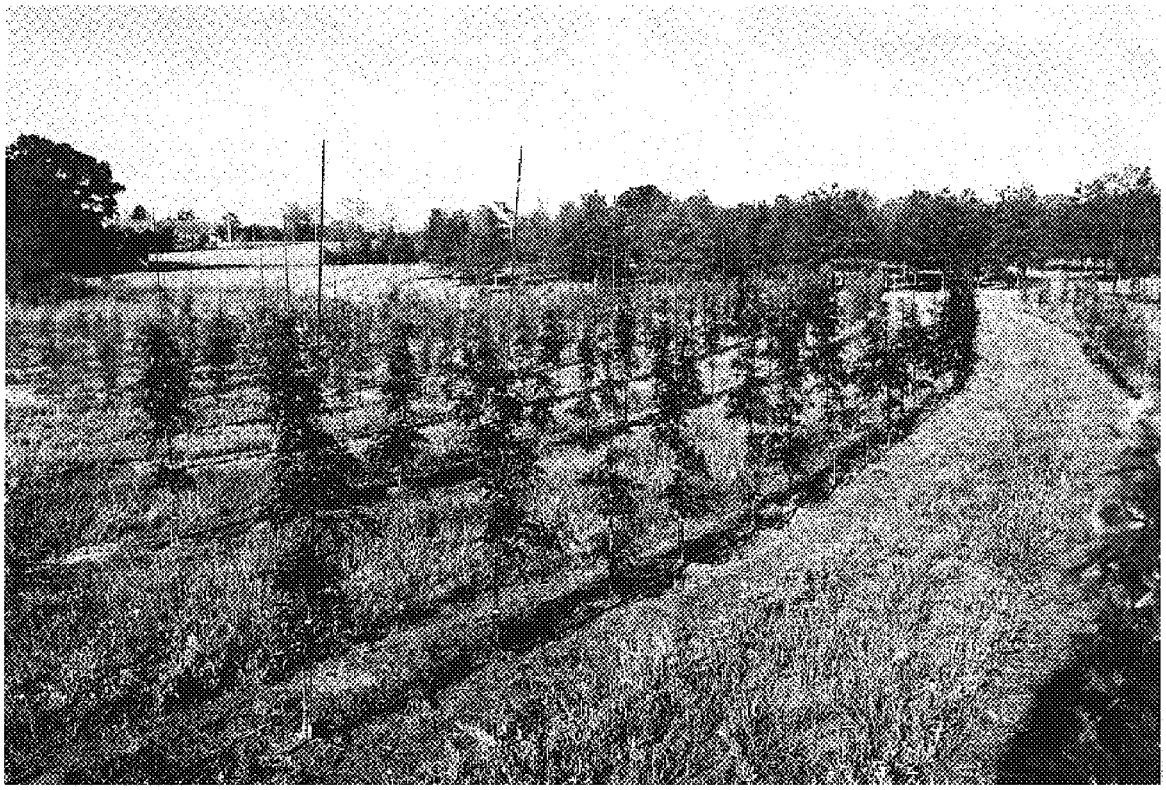
FIG. 3 taken during the spring of 2006 shows the progeny of the claimed cultivar.
Figure 4:
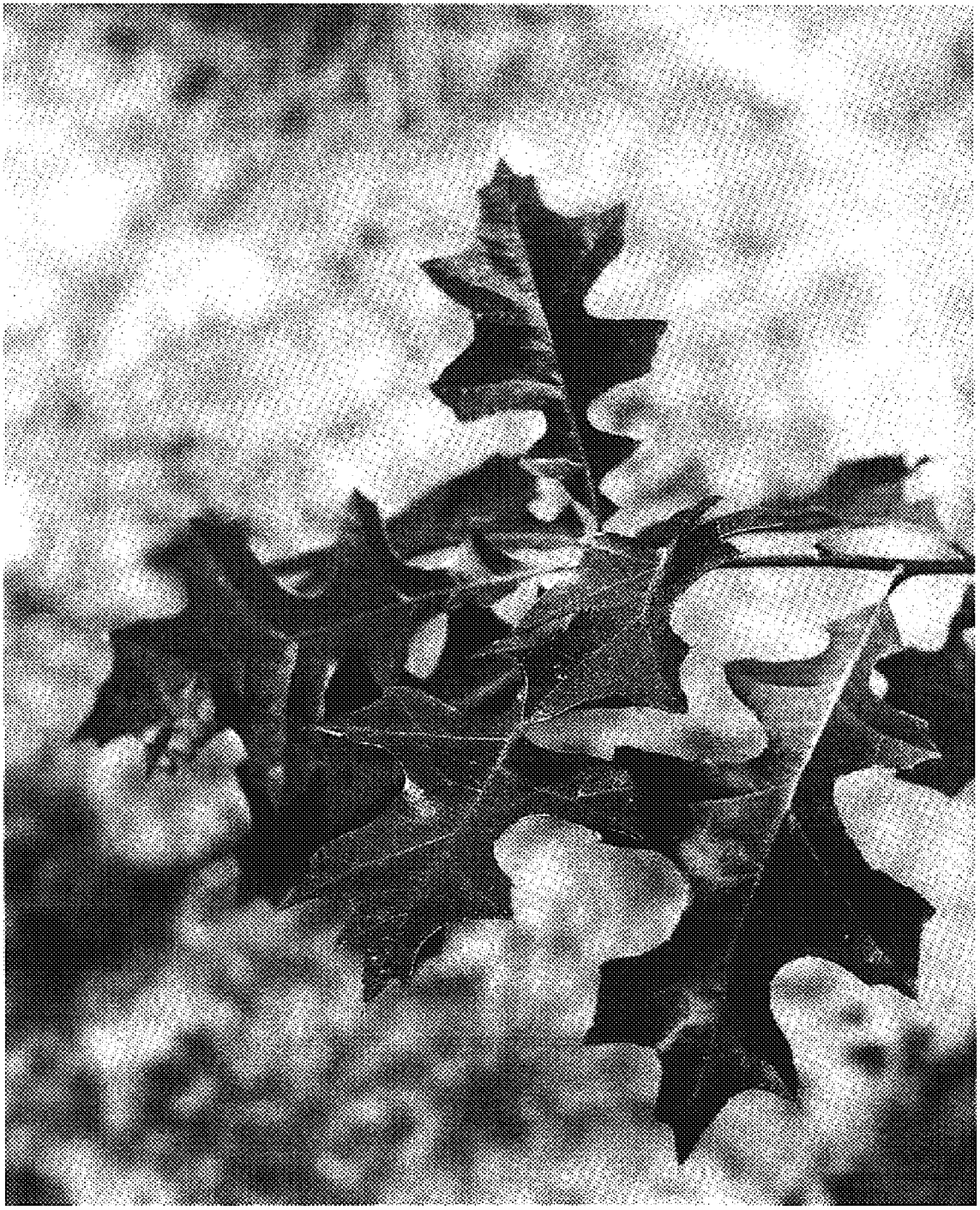
FIG. 4 shows the new growth foliage of the claimed cultivar.
Figure 5:
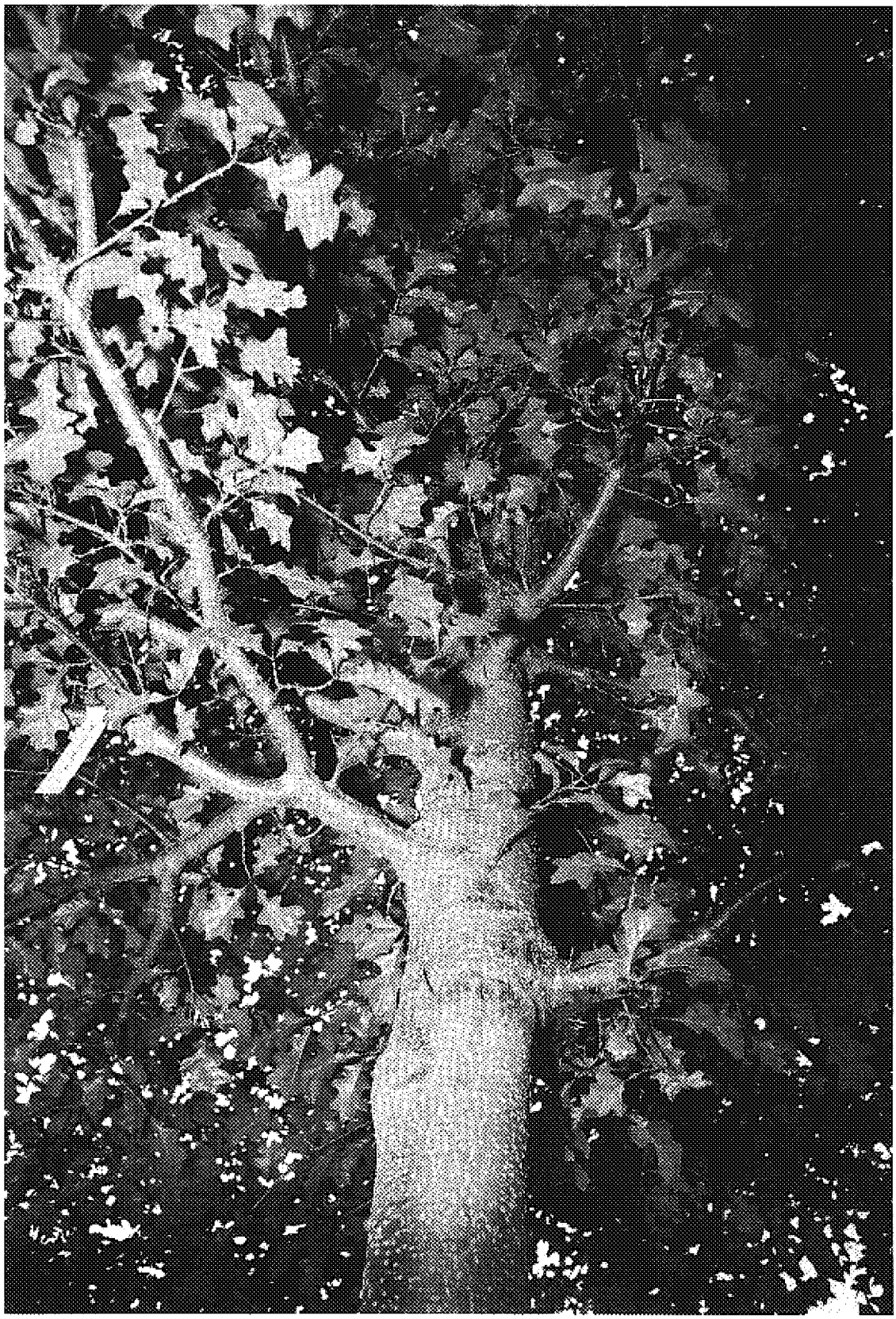
FIG. 5 shows the internal canopy of the claimed cultivar.

The following is a detailed description of 'QNMTF' Nuttall oak tree with color terminology in accordance with the Royal Horticultural Society (R.H.S.) Colour Chart except where the context indicates a term having its ordinary dictionary meaning.

The claimed cultivar has not been observed under all growing conditions, and variations may occur as a result of different growing conditions. All progeny of the claimed cultivar, insofar as have been observed by the inventor, have remained genetically stable in all characteristics described hereinafter. Other than as set out hereinafter, as of this time, no other characteristics have been observed by the inventor which are different from common Nuttall oak trees.

Parentage: Naturally occurring cross-pollinated seedling of *Quercus nuttallii* grown from bare-root liner purchased in the winter of 2001 from a nursery in Florida.

Locality where grown and observed: 'QNMTF' Nuttall oak trees are currently in production in a production field in Loganville, Walton County, Ga. This area of Walton County has a clay loam soil type with rainfall that varies between 30" inches, and 60" inches annually. This particular area is located in USDA Hardiness Zone 7.

Size and growth rate: The original tree, aged 5 years measured 6.25" inches caliper at 12" inches above the ground. The height of 24' feet and spread of 13' feet provides a 1.85 to 1 height to width ratio. Average caliper growth rate is between 1.00" inches to 1.25" inches per year.

Foliage: Typical of the species, alternate, simple, obovate to elliptic, 3.5" inches wide by 6.0" inches long. The new growth is grayed-purple like (RHS 183A). Mature foliage is dark green above like (RHS 137A) and lighter green below like (RHS 137C). The fall color is orange-red ranging from (RHS N30A) to (RHS 33B). The petiole is 0.5" inch to 0.75" long and grayed-purple like (RHS 183B).

Buds: Imbricate, ⅛" inch to ¼" inch long, ovoid, sharp-pointed, reddish like (RHS 46B).

Flowers: Typical of species. Flowers are borne in clustered catkins in early April, usually lasting for 10 to 14 days.

Fruit: Typical of the species being ovate 1.0" inch to 1/25" inch long and 0.5" inch to 0.6" inch wide and grayed-orange in color like (RHS 177A). The cap covered slightly more than one-third of the fruit and was light brown like (RHS 199B).

Trunk: Typical of the species. In youth the bark is smooth, gray, becoming gray-green like (RHS 198A) with patches/striations of grayed-green like (RHS 195A).

Branching: Slightly ascending to nearly horizontal at the base, emerging at 80 to 90 degrees from the trunk. Upper branches are more ascending, emerging at 45 degrees or more from the trunk. Color is gray-green (RHS 198A).

Shade: Compact, pyramidal with dense branching and dominant central leader.

Root System: Fibrous, typical of *Quercus nuttallii.*

Vigor: The initially discovered tree has averaged between 1.0" inch to 1.25" inch in caliper growth per year. The root development from time of softwood cuttings to a finished rooted 3½" inch pot is five to seven weeks.

Disease: Free from disease.

Pests: Displays spider mite resistance but does show signs of mild leaf hopper damage.

What is claimed is:

1. A new and distinct variety of Nuttall oak tree named 'QNMTF' substantially as herein shown, illustrated and described, characterized particularly as to novelty by its compact habit with dense canopy, vigorous growth rate and burgundy new growth that matures to dark green color in summer and orange-red color in fall.

* * * * *

UNITED STATES PATENT AND TRADEMARK OFFICE

CERTIFICATE OF CORRECTION

PATENT NO. : PP 20,550 P2
APPLICATION NO. : 11/818773
DATED : December 15, 2009
INVENTOR(S) : Dwayne C. Moon It is certified that error appears in the above-identified patent and that said Letters Patent is hereby corrected as shown below:

Col. 3, Line 52
Replace "cultivar"
with --cultivar--

Signed and Sealed this

Twentieth Day of April, 2010

David J. Kappos

David J. Kappos
*Director of the United States Patent and Trademark Office*

UNITED STATES PATENT AND TRADEMARK OFFICE

CERTIFICATE OF CORRECTION

Figure 6:
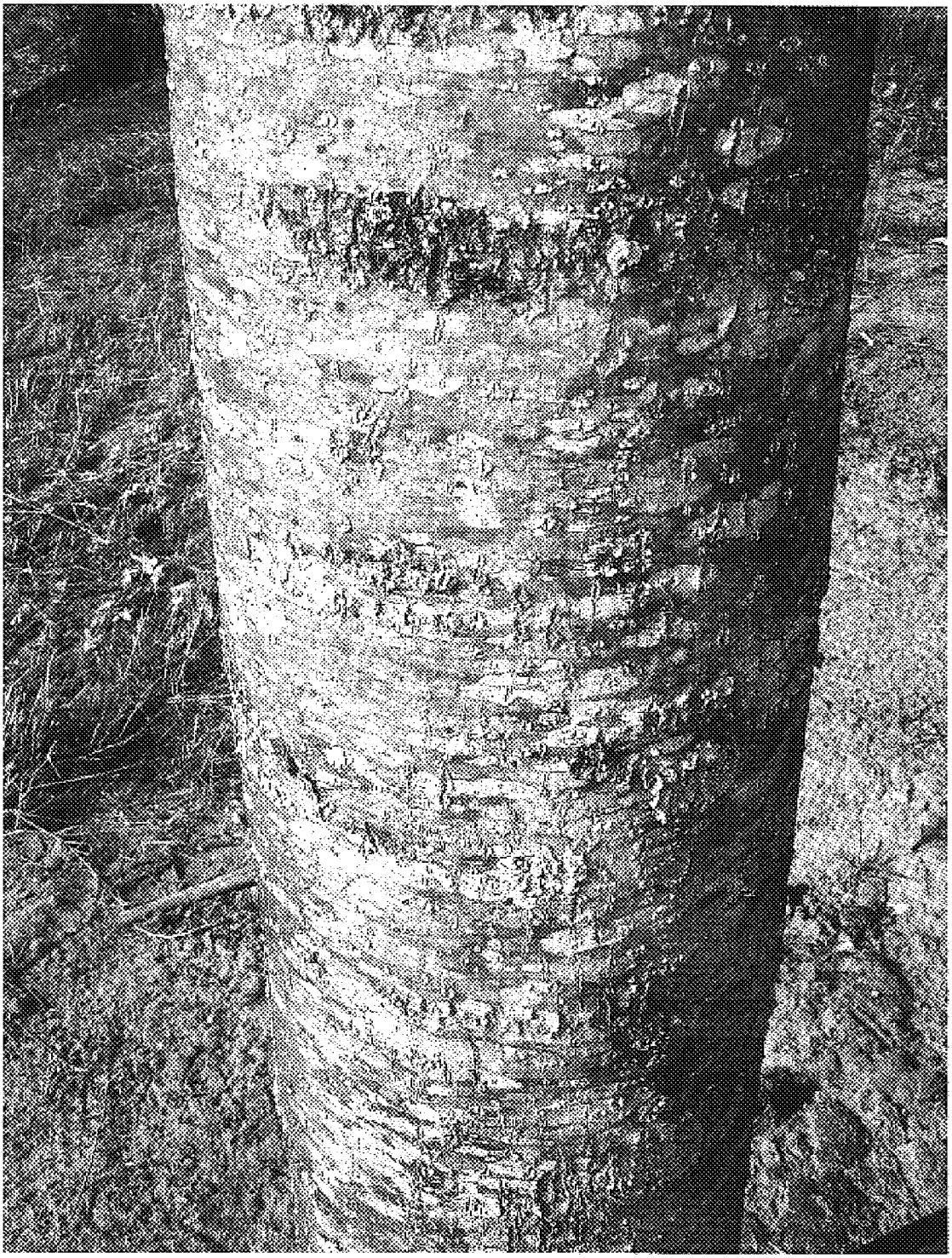
FIG. 6 shows the trunk of the claimed cutlivar.
Figure 7:
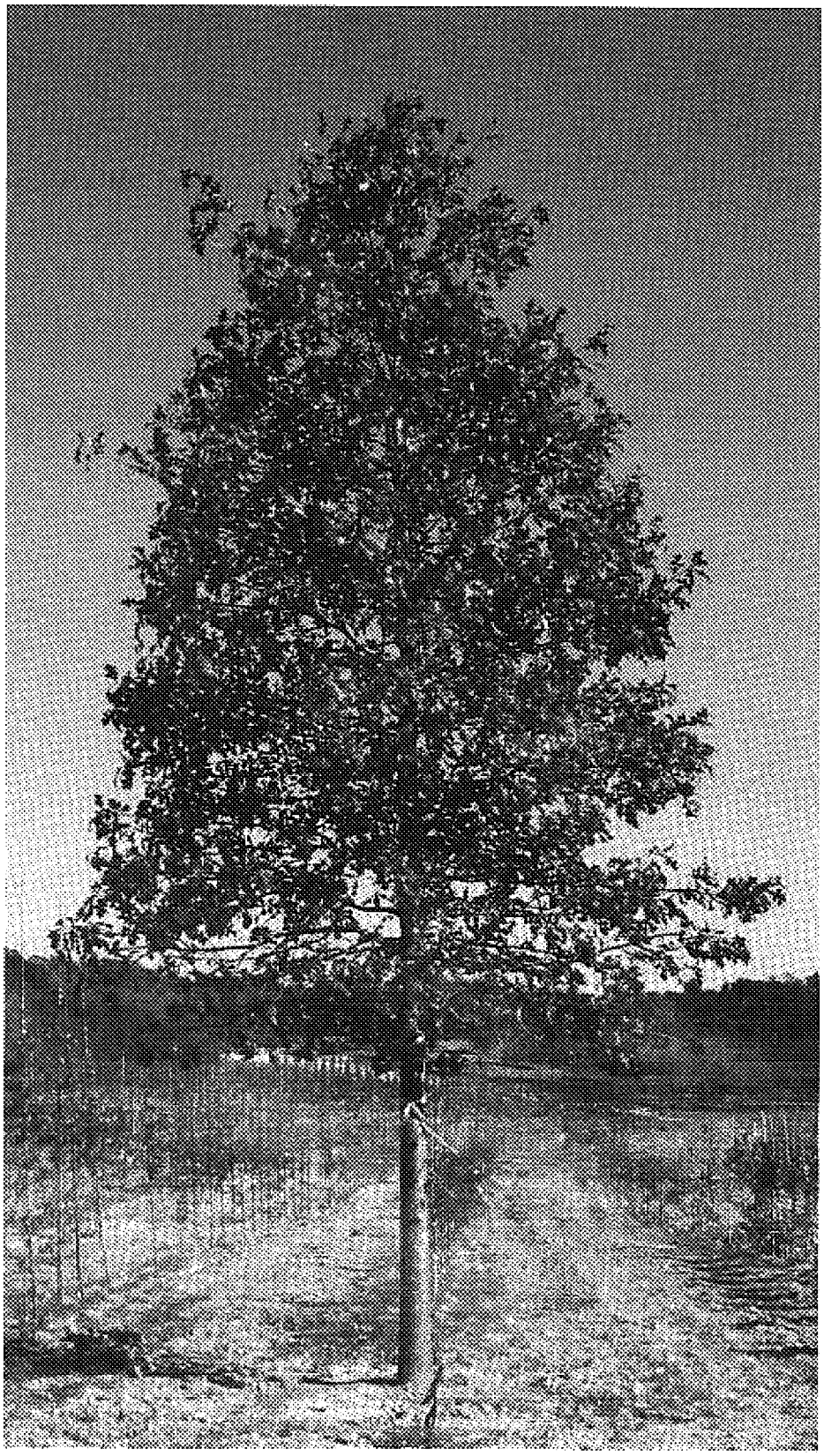
FIG. 7 taken in November 2006 shows the overall fall color of the claimed cultivar.
Figure 8:
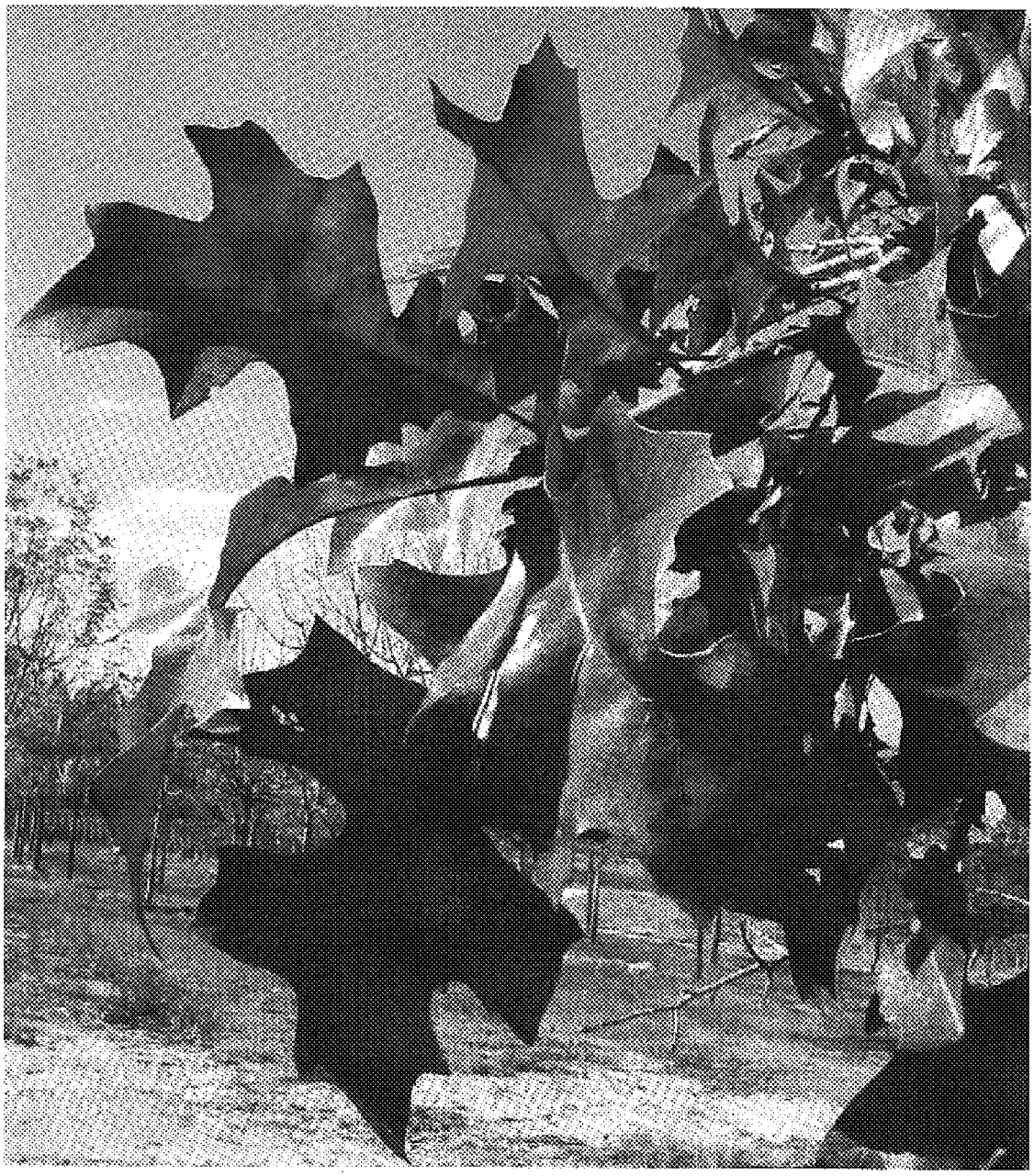
FIG. 8 shows a close up of the fall color of the claimed cultivar.

PATENT NO. : PP 20,550 P2
APPLICATION NO. : 11/818773
DATED : December 15, 2009
INVENTOR(S) : Dwayne C. Moon It is certified that error appears in the above-identified patent and that said Letters Patent is hereby corrected as shown below:

Col. 3, under Brief Description Of The Drawings, Line 53, for describing Fig. 6,
After the word "claimed" delete "cutlivar"
Replace with --cultivar--

Signed and Sealed this

First Day of June, 2010

David J. Kappos

David J. Kappos
*Director of the United States Patent and Trademark Office*